(12) United States Patent
Dunklau et al.

(10) Patent No.: US 9,532,566 B1
(45) Date of Patent: Jan. 3, 2017

(54) ULTRA LOW VOLUME FOGGER

(71) Applicants: Caralyn Dunklau, Delevan, WI (US); Dana Dunklau, Delevan, WI (US)

(72) Inventors: Caralyn Dunklau, Delevan, WI (US); Dana Dunklau, Delevan, WI (US)

( * ) Notice: Subject to any disclaimer, the term of this patent is extended or adjusted under 35 U.S.C. 154(b) by 189 days.

(21) Appl. No.: 14/464,810

(22) Filed: Aug. 21, 2014

(51) Int. Cl.
| | |
|---|---|
| *B01F 3/04* | (2006.01) |
| *A01N 25/18* | (2006.01) |
| *B05B 7/00* | (2006.01) |
| *A01M 1/20* | (2006.01) |

(52) U.S. Cl.
CPC ............ *A01N 25/18* (2013.01); *A01M 1/2044* (2013.01); *B01F 3/04056* (2013.01); *B05B 7/00* (2013.01); *A01M 1/2033* (2013.01)

(58) Field of Classification Search
CPC ..... B01F 3/04; B01F 3/04049; B01F 3/04056; B01F 3/04007; B01F 3/04014; B01F 3/04021; A01M 1/2022; A01M 1/2033

USPC ........................ 261/34.1, 36.1, 72.1, 78.2, 66
See application file for complete search history.

(56) References Cited

U.S. PATENT DOCUMENTS 3,548,151 A * 12/1970 Jung ...................... A01M 13/00
239/133
5,248,448 A * 9/1993 Waldron ................... B05B 7/10
239/338

\* cited by examiner

*Primary Examiner* — Robert A Hopkins
(74) *Attorney, Agent, or Firm* — G. Brian Pingel; David M. Breiner; BrownWinick Law Firm

(57) ABSTRACT

Disclosed is a system that may include a holding tank configured to hold a liquid, a pump configured to receive the liquid from the holding tank, a nozzle configured to emit a fog, and a fan configured to push the fog through a tube. Disclosed also is a method of creating a fog by transferring a liquid from a holding tank to a pump, pumping the liquid to a pressure regulator, moving the liquid from the pressure regulator back to the holding tank when a pressure is above a first value and moving the liquid to a fogger when the pressure is below the first pressure.

16 Claims, 5 Drawing Sheets

ULTRA LOW VOLUME FOGGER

BACKGROUND

1. Field

Example embodiments relate to a system configured to emit a fog and a method of producing a fog. In example embodiments the fog may include, but is not required to include, an insecticide, a disinfectant, and/or an antimicrobial agent. Example embodiments also relate to a method of applying a fog to a relatively large area.

2. Description of the Related Art

Ultra low volume (ULV) cold aerosol fog refers to a droplet size that is less than 30 microns. Droplets of this size have been shown to have optimum drift. There are several methods available for creating a ULV fog. First, a low pressure high volume air flow may be forced over itself. Liquid may be injected into a point where the air flow comes together just in front of a nozzle. The turbulence breaks the liquid into an ULV fog. This method requires a gas motor and a blower of some sort. Another method of creating an ULV fog is to use high pressure low volume liquid which is typically found in a paint sprayer. In this latter method, high pressure air blasts come together in front of a liquid injector and the liquid is blasted into a fog. This method requires a gas engine and a compressor. Another method uses a rotary atomizer. This method utilizes pores in a head that spins at about 30,000 rpm. The product is injected into a center of the head, is spun through a nozzle, and is then moved by a fan. A problem with this latter embodiment is that it requires a relatively delicate electrical system which is expensive and which breaks down often.

SUMMARY

Applicant notes that conventional art foggers configured to generate ULV fog have several drawbacks. As such, Applicant set out to devise a fogger which does not suffer the drawbacks associated with the prior art. As a consequence, Applicant has designed a new and nonobvious fogger capable of generating a ULV fog which is robust and relatively inexpensive.

Example embodiments relate to a system configured to emit a fog and a method of producing a fog. In example embodiments the fog may include, but is not required to include, an insecticide, a disinfectant, and/or an antimicrobial agent. Example embodiments also relate to a method of applying a fog to a relatively large area.

In accordance with example embodiments, a system may include a holding tank configured to hold a liquid, a pump configured to receive the liquid from the holding tank, a nozzle configured to emit a fog, and a fan configured to push the fog through a tube. In example embodiments, the system may include a recirculation line allowing a portion of the liquid may be diverted to the holding tank. In example embodiments, the system may include a pump that starts and stops to maintain a given pressure. In this latter case, there may be no need to divert any portion of the product back to the holding tank.

In accordance with example embodiments, a method of creating a fog may include transferring a liquid from a holding tank to a pump, pumping the liquid to a pressure regulator, moving some of the liquid from the pressure regulator back to the holding tank when a pressure is above a first value and moving the liquid to a fogger when the pressure is below the first value, and creating a fog.

BRIEF DESCRIPTION OF THE DRAWINGS

Example embodiments are described in detail below with reference to the attached drawing figures, wherein:

FIG. 3 is a view of the system in accordance with example embodiments showing liquid flowing through the system when an on/off valve is on;

DETAILED DESCRIPTION

Figure 1:
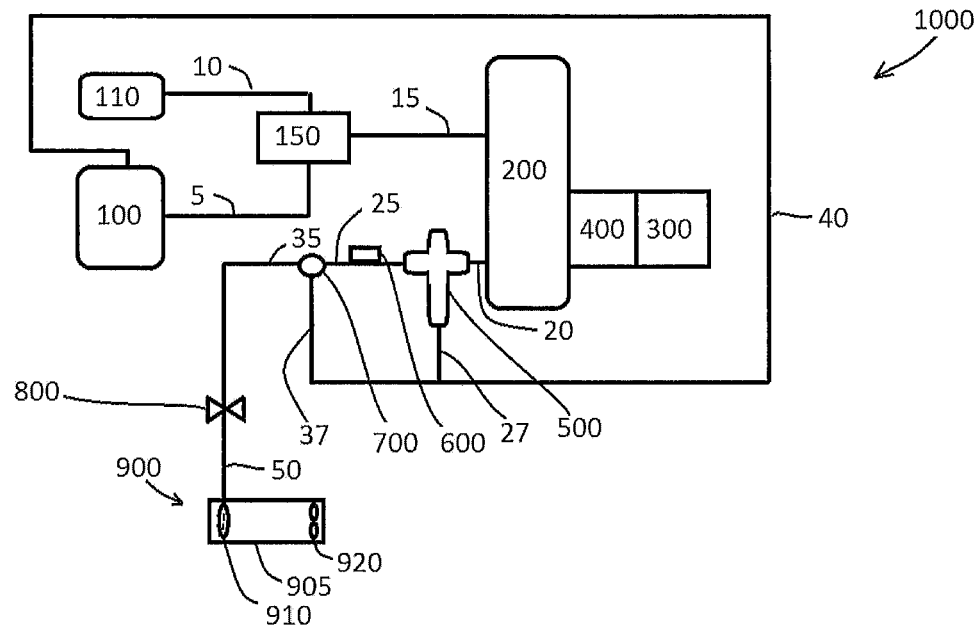
FIG. 1 is a view of a system in accordance with example embodiments.
Figure 2:
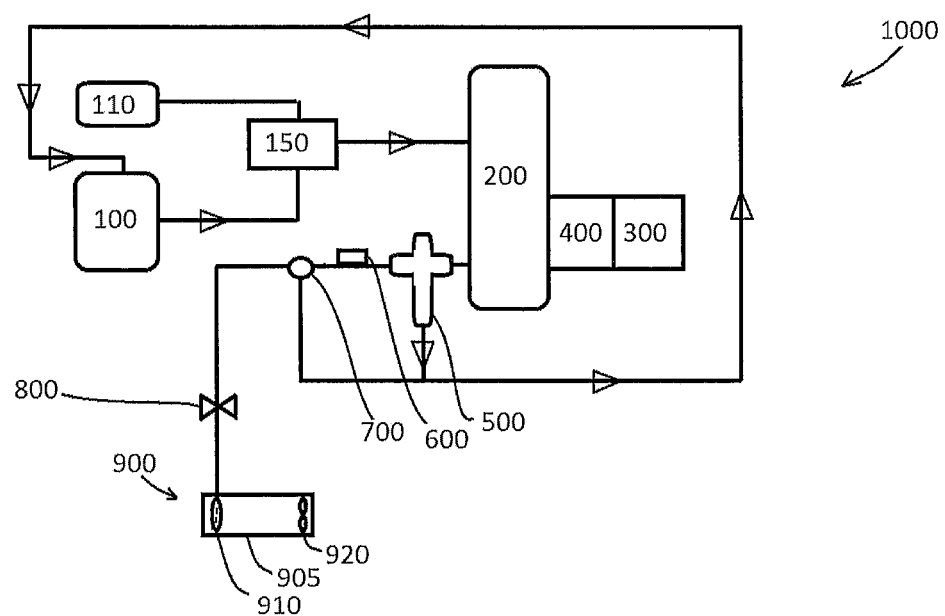
FIG. 2 is a view of the system in accordance with example embodiments showing liquid flowing through the system when an on/off valve is off.
Figure 3:
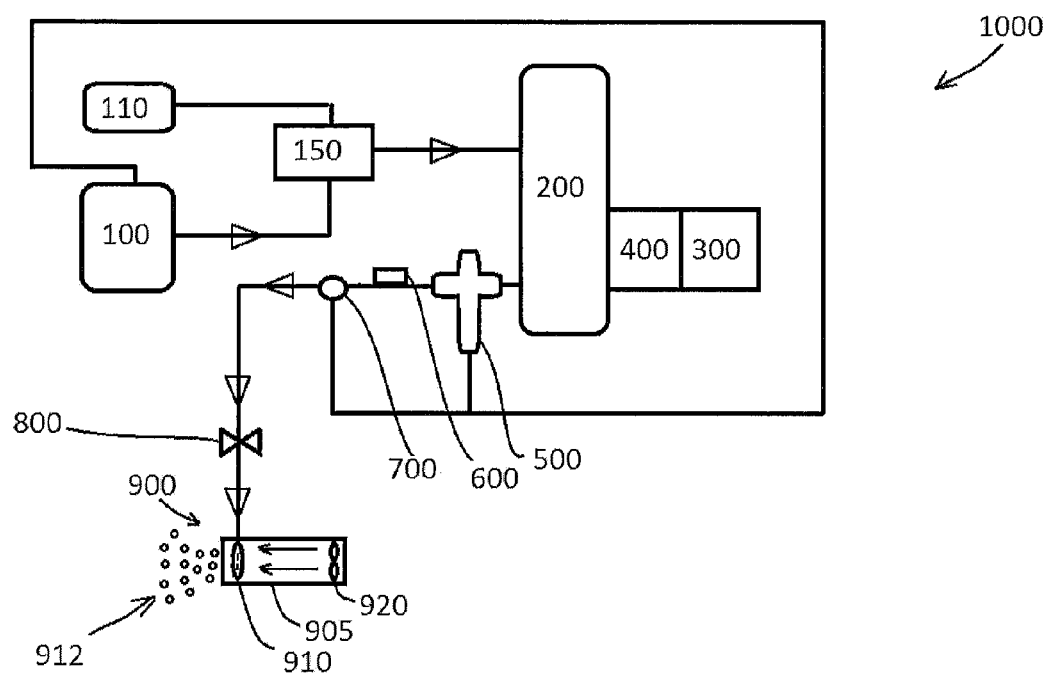
Figure 4:
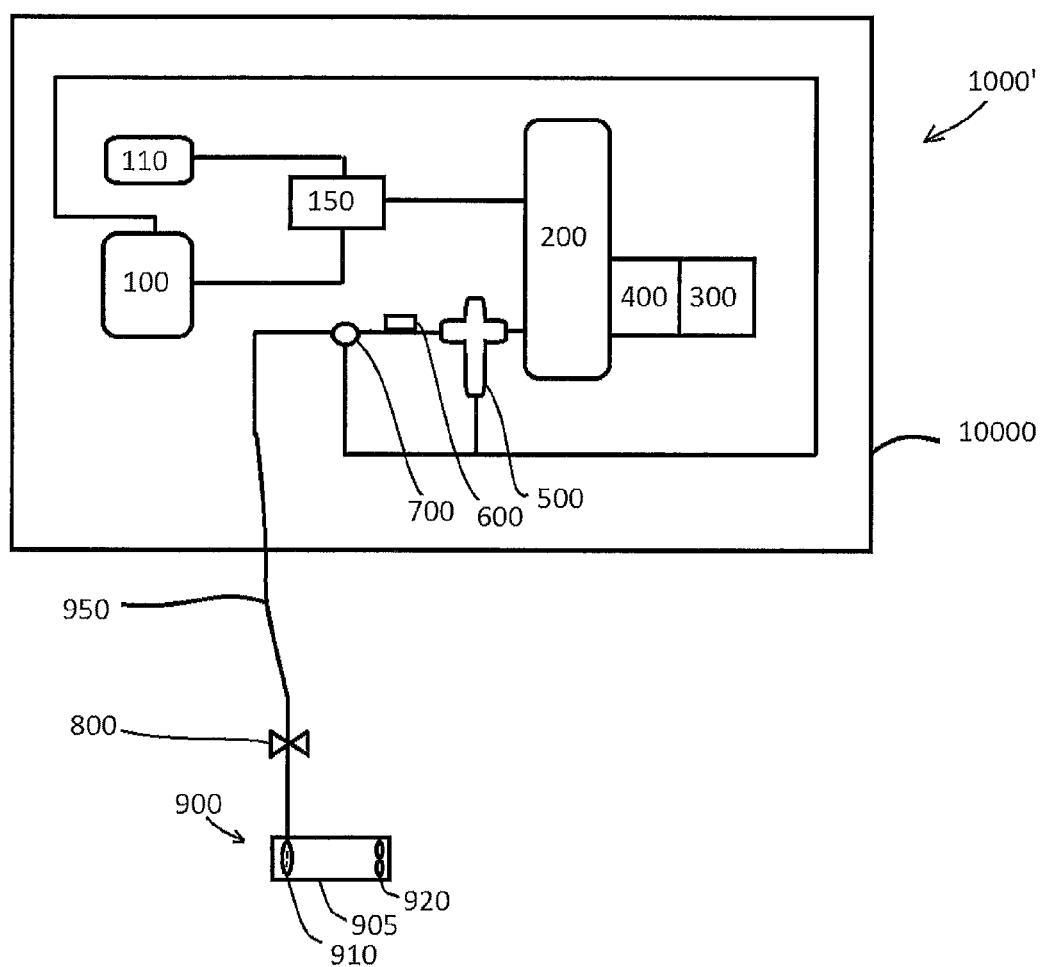
FIG. 4 is a view of another system in accordance with example embodiments.
Figure 5:
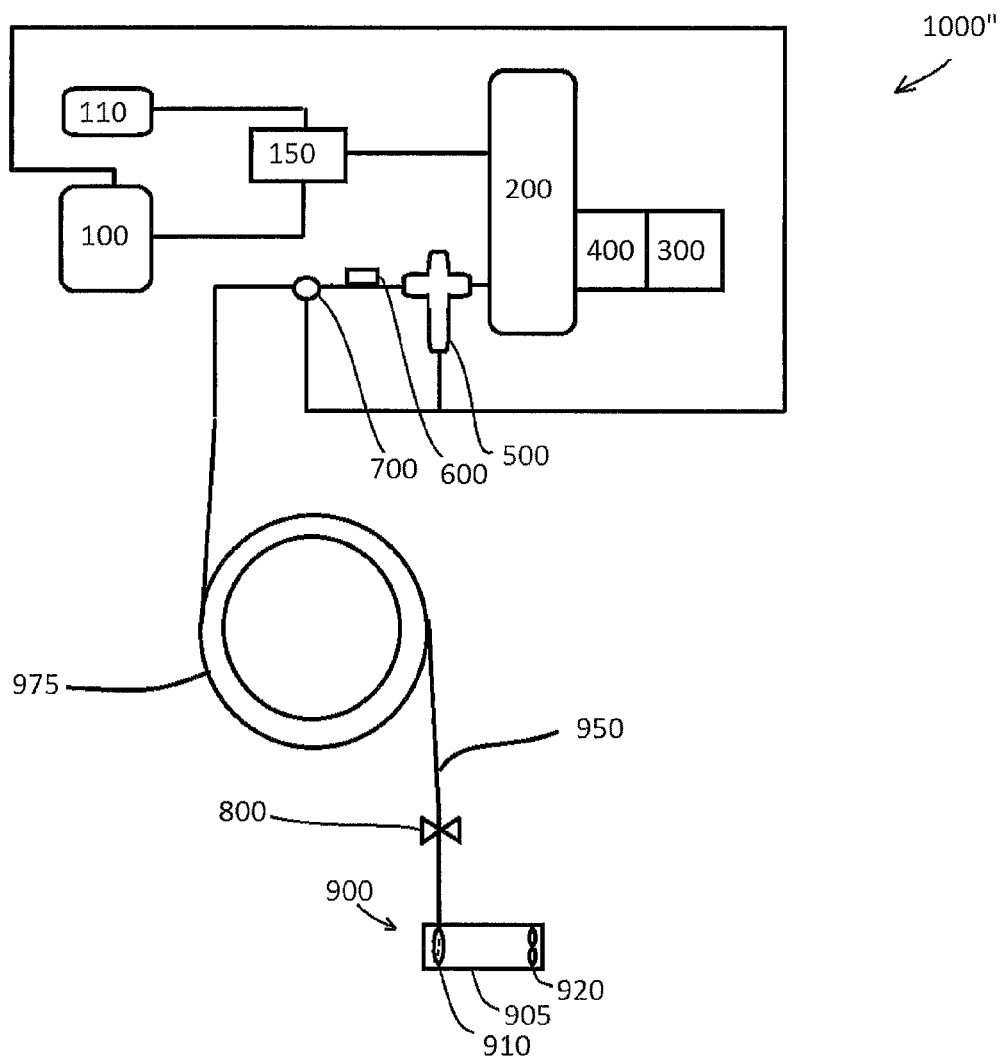
FIG. 5 is a view of another system in accordance with example embodiments.
Figure 6:
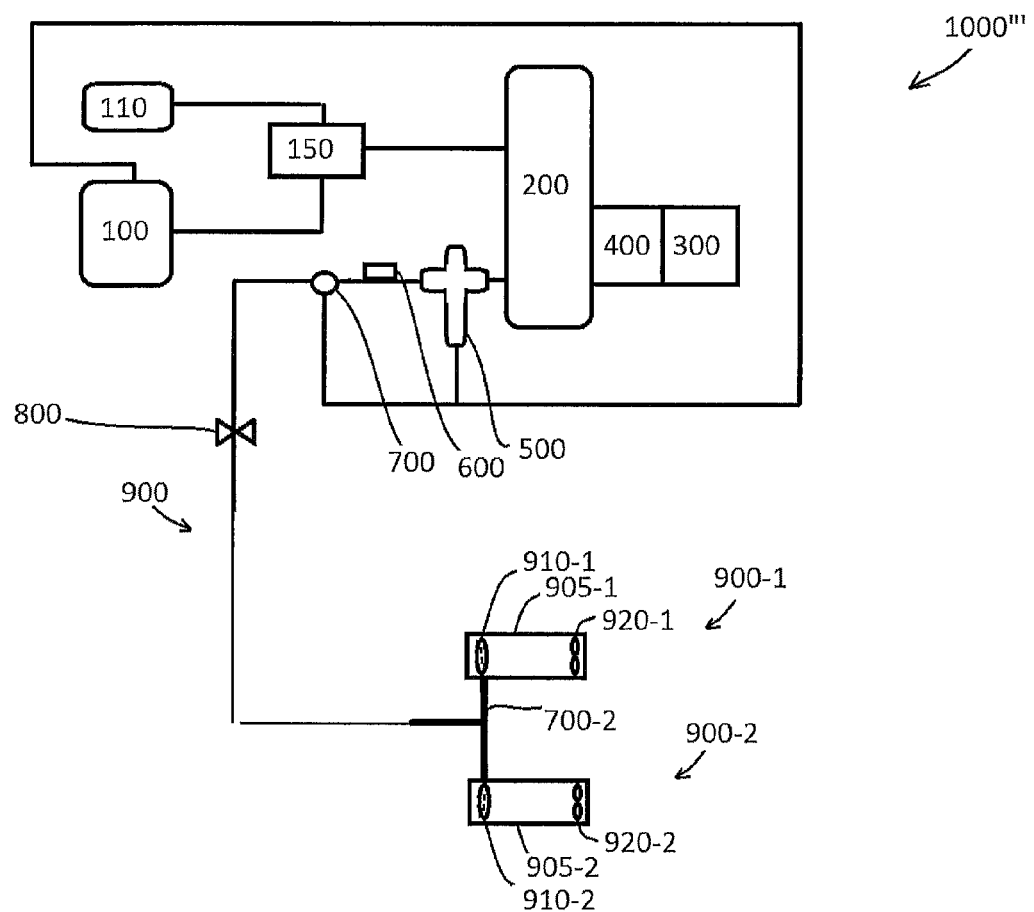
FIG. 6 is a view of another system in accordance with example embodiments.

Example embodiments will now be described more fully with reference to the accompanying drawings. Example embodiments are not intended to limit the invention since the invention may be embodied in different forms. Rather, example embodiments are provided so that this disclosure will be thorough and complete, and will fully convey the scope of the invention to those skilled in the art. In the drawings, the sizes of components may be exaggerated for clarity.

In this application, when an element is referred to as being "on," "attached to," "connected to," or "coupled to" another element, the element may be directly on, directly attached to, directly connected to, or directly coupled to the other element or may be on, attached to, connected to, or coupled to any intervening elements that may be present. However, when an element is referred to as being "directly on," "directly attached to," "directly connected to," or "directly coupled to" another element or layer, there are no intervening elements present. In this application, the term "and/or" includes any and all combinations of one or more of the associated listed items.

In this application, the terms first, second, etc. are used to describe various elements and components. However, these terms are only used to distinguish one element and/or component from another element and/or component. Thus, a first element or component, as discussed below, could be termed a second element or component.

In this application, terms, such as "beneath," "below," "lower," "above," "upper," are used to spatially describe one element or feature's relationship to another element or feature as illustrated in the figures. However, in this application, it is understood that the spatially relative terms are intended to encompass different orientations of the structure. For example, if the structure in the figures is turned over, elements described as "below" or "beneath" other elements would then be oriented "above" the other elements or features. Thus, the term "below" is meant to encompass both an orientation of above and below. The structure may be otherwise oriented (rotated 90 degrees or at other orientations) and the spatially relative descriptors used herein interpreted accordingly.

Example embodiments are illustrated by way of ideal schematic views. However, example embodiments are not intended to be limited by the ideal schematic views since example embodiments may be modified in accordance with manufacturing technologies and/or tolerances.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, example embodiments relate to a system configured to emit a fog and a method of producing a fog. In example embodiments the fog may include, but is not required to include, an insecticide, a disinfectant, and/or an antimicrobial agent. Example embodiments also relate to a method of applying a fog to a relatively large area.

FIG. 1 is a view of a system 1000 in accordance with example embodiments. In example embodiments, the system 1000 may include a holding tank 100, a pump 200, an actuator 300, a mechanism 400 between the actuator 300 and the pump 200, a pressure regulator 500, a pressure switch 600, a pressure dump return valve 700, an on/off valve 800, and a fogger 900. The fogger 900, for example, may include a tube 905, a nozzle manifold 910 in the tube 905, and fan 920 in the tube 905. In example embodiments, the various elements of the system 1000 may be interconnected via a plurality of tubes and/or pipes 5, 10, 15, 20, 25, 27, 35, 37, 40, and 50. For example, in example embodiments, the plurality of tubes and/or pipes 5, 10, 15, 20, 25, 27, 35, 37, 40, and 50 may interconnect, at least, the holding tank 100, the pump 200, the pressure regulator 500, the pressure dump relief valve, the off/on valve 800, and the fogger 900.

In example embodiments the holding tank 100 may be configured to store a liquid. In example embodiments, the liquid may include, but is not required to include, an insecticide, a disinfectant, and/or an antimicrobial agent. In example embodiments, the liquid, for example may include a pesticide for killing a type of insect, for example, a mosquito and/or a fly. In example embodiments, the liquid may include a natural pyrethrum or synthetic pyrethroid such as permethrin, deltamethrin, bifenthrin, fluvalinate, fenvalerate, esfenvalerate, lambda cyhalothrin, tetramethrin, tralomethrin, cyfluthrin, resemethrin, sumithrin, imiprothrin, prallethrin (ETOC®), allethrin, bioallethrin, esbiothrin, s-bioallethrin (ESBIOL®), d-allethrin; cypermethrin; isomeric forms thereof such as zeta cypermethrin and tau fluvalinate; channel blocking insecticide such as a phenyl pyrazole (fipronil); acetylcholinesterase inhibitor such as a carbamate (carbaryl and bendiocarb); oxadiazines such as indoxacarb; organophosphate such as a chlorpyriphos (DURSBAN®) and acephate (ORTHENE®); neonicotinoid insecticide such as dinotefuran (SHURIKEN®); thiamethoxam; imidacloprid; acetamiprid; thiacloprid; clothianidin; nitenpyran; insect growth regulator such as benzoylphenyl urea (such as diflubenzuron (DIMILIN®), teflubenzuron, flufenoxuron, bistrifluoron, hexaflumuron; juvenile hormone mimic such as pyriproxifen (SUMILARV®), methoprene and fenoxycarb; fermentation insecticide such as abamectin, spiromesifen, spinosad and *Bacillus thuringiensis*; plant oil insecticide such as cinnamon, rosemary, wintergreen, citrus and clove oils; acaracide; miticide; fungicide; herbicide and combinations thereof. Disinfectants or pesticides that exhibit advantageous results with the system 1000 and are currently in the marketplace are formaldehyde, oxine, Synergize, Tek-trol, Bio-Phene, Virkons, Virocid and 904, n-Alkyl (60% C14, 30% C16, 5% C12, 5% C18) Dimethyl benzyl ammonium chloride (Amount 2.25%) n-Alkyl (68% C12, 32% C14) Dimethyl benzyl ammonium chloride (Amount 2.25%); 3-(trimethoxysilyl) propyl dimethyl octadecyl ammonium chloride CAS #27668-52-6; Alkenyl* dimethyl ammonium chloride *(75% C18', 25% C16'); Alkyl dimethyl ethylbenzyl ammonium cyclohexyl sulfamate CAS#71808-54-3 CAS#37335-68-5; Alkyl trimethyl ammonium bromides CAS#68424-92-0; Alkyl* dimethyl benzyl ammonium chloride *(41% C14, 28% C12, 19% C18, 12% C16 CAS#68391-01-5; Decyl-N-methyl-N-(3-trimethoxysilyl)propyl)-1-decanaminium chloride CAS#68959-20-6; Diallyl dimethyl ammonium chloride polymers CAS#26062-79-3; Didecyl dimethyl ammonium chloride CAS#7173-51-5; Dodecylbenzyl trimethyl ammonium chloride CAS#1330-85-4; N-isononyl-N, N-dimethyl decanaminium chloride CAS#138698-36-9; Octyl decyl dimethyl ammonium chloride CAS#32426-11-2; Oxydiethylene bis(alkyl dimethyl ammonium chloride), alkyl derived from coconut oil fatty acids CAS#68607-28-3; Tetradecyl dimethyl benzyl ammonium chloride CAS#139-08-2; Ortho-benzyl-para-chlorophenol CAS#120-32-1; Ortho-benzyl-para-chlorophenol, sodium salt CAS#3184-65-4; Para-chloro-meta-cresol CAS#59-50-7; Sodium p-chloro-m-cresolate CAS#15733-22-9; Triclosan CAS#3380-34-5; Naled (1,2-dibromo-2,2-dichloroethyl dimethyl phosphate); and Hydrogen Peroxide.

In example embodiments a selector 150, for example, a three way selector unit, may be arranged between the pump 200 and the holding tank 100. In example embodiments, the selector 150 may be configured to receive a liquid from the holding tank 100 and a second tank 110. In example embodiments the second tank 110 may be, but is not required to be, a flush tank. In example embodiments the selector 150 may control which liquid, from either one of the holding tank 100 and the second tank 110, is delivered to the pump 200. In normal operation the selector unit 150 delivers liquid from the holding tank to the pump 200, however, the selector unit 150 may alternatively control liquid to flow from the second tank 110 to the pump 200.

In example embodiments the pump 200 may pump the liquid from either the holding tank 100 or the second tank 110 through the system 1000. In example embodiments, the pump 200 may be, but is not required to be, a high pressure pump capable of pumping the fluid at a fairly high pressure, for example, between about 0 and 3000 psi. In example embodiments the pump 200 may be driven by the actuator 300. In example embodiments, the actuator 300 may be, but is not required to be, an electric motor, gas motor or a hydraulic motor. For example, the actuator 300 may be an electric motor configured to run on AC or DC power. The purpose of the actuator 300 is to apply a force and/or a torque to the pump 200 to operate/actuate the pump 200. In example embodiments the system 1000 may further include the mechanism 400 between the actuator 300 and the pump 200. In example embodiments the mechanism may be, but is not required to be, a gear box which controls the operation of the pump 200 by the actuator 300.

In example embodiments liquid flowing out of the pump 200 may flow into the pressure regulator 500, which may be, but is not required to be, a T valve. In example embodiments, the pressure regulator 500 may have a set pressure which, if exceeded, may cause the liquid flowing from the pump 200 to be diverted to the holding tank 100 via a return line 40. In example embodiments, the set pressure of the regulator may be about 250 psi to about 3000 psi. If the pressure in the pressure regulator 500, however, is below the set pressure, the liquid may flow from the pressure regulator 500 to the pressure dump return valve 700. In example embodiments, the pressure dump return valve 700 may be opened to send liquid back to the holding tank 100 via the return line 40. In example embodiments opening the pressure dump return valve 700 may reduce pressure in the system which may aid in priming the pump 200. Though a presence of the pressure dump return valve 700 in the system 1000 is not critical, its presence may allow for the pump 200 to prime without having to adjust the pressure regulator 500. In the event the pump 200 is primed, the pressure dump return valve 700 may be closed and liquid may flow towards the on/off valve 800 and then to the fogger 900.

In example embodiments, a pressure switch 600 may be placed between the pump 200 and the fogger 900, for example, between the pressure dump return valve 700 and the pressure regulator 500. In example embodiments, the pressure switch 600 may be in communication with a pressure sensing device which may sense a pressure of the liquid leaving the pump 200. In example embodiments, if the pressure of the liquid leaving the pump 200 is too high, for example, above the maximum working pressure of the system 1000 but below the below the maximum safe operating pressure, then the pressure switch 600 may shut the pump 200 off. As such, the pressure switch 600 may provide a safeguard against a generation of too much pressure from the pump. Applicant notes that while the pressure switch 600 of system 1000 provides a safety feature, its presence is not critical and therefore may be omitted.

In example embodiments, when the on/off valve 800 is on, the liquid may flow to the nozzle manifold 910 where the liquid is atomized to form a plurality of droplets 912 having an average size of about 30 microns or less. As such, the nozzle manifold 910 may form a fog within the tube, 905 of the fogger 900. This tube, 905 may or may not be necessary. The ULV fog producing nozzles that create droplets less than 30 microns in diameter may or may not be mounted directly to the front of a fan. In example embodiments, the fog may be blown out of the tube 905 by the fan 920. Thus, in example embodiments, as the liquid is fed to the nozzle manifold 910 a fog may be created by the nozzle manifold 910 which may be blown out of the tube 905 by the fan 920. In the event the nozzles are mounted directly in front of the fan, 920 the fog will be blown away from the fan.

In example embodiments, the pressure of the liquid in the tube 50 may be, but is not required to be, in the range of about 0 to about 3000 psi. In this pressure range a suitable nozzle 910 designed to convert high pressure liquid to fog using pressure alone, for example, a Bete-PJ8 nozzle, may be used to create the aforementioned fog. The invention, however, is not limited by the above pressure range or the example nozzle manifold 910 as a variety of nozzle manifolds 910 may be used with a variety of pressure ranges.

FIG. 2 is a view of the system 1000 illustrating the on/off valve 800 turned off. In this configuration liquid may not pass through the on/off valve 800. As a consequence all of the liquid being pumped by the pump 200 may be recirculated to the holding tank 100 via tubes 20, 27, and 40.

FIG. 3 is a view of the system 1000 illustrating the on/off valve 800 turned on. In this configuration the liquid from the pump 200 may flow through the on/off valve 800 and to the nozzle manifold 910 where it may be atomized into the fine droplets 912 having a diameter of about 30 microns or less. As shown in FIG. 3, the fine droplets 912 may be blown out of the tube 905 via the fan 920. Although FIG. 3 illustrates some of the liquid flowing from pump 200 to the nozzle manifold 910, it is understood that some of the liquid may actually return to the holding tank 100 via the pipes and or tubes 27 and 40 since liquid flowing through the pressure regulator 500 will tend to flow in a direction of least resistance. In other words, when the on/off valve 800 is in the on state, the liquid may be diverted to the nozzle manifold 910 tubes and/or pipes 20, 25, 35, and 50 until pressure builds up to the same pressure that the system 1000 (for example, the set pressure of the regulator 500) has been set to at which point liquid may flow to the holding tank 100. Though the system 1000 can continue to build pressure, the pressure regulator 500 will divert liquid back to the holding tank 100 in order to maintain a constant pressure. As such, the systems of FIGS. 1-3 are constant pressure systems.

In example embodiments the system 1000 may be embodied in several forms. For example, as a first embodiment, the system 1000 may be configured such that each of the components are fixed in a position, for example, by permanently mounting each of the elements of the system 1000 to a frame. On the other hand, only some of the elements of the system 1000 may be permanently associated with a frame. For example, as shown in FIG. 4, each of the tank 100, the pump 200, the motor 300, the mechanism 400, and the pressure regulator 500 may be fixed to a frame 10000 and the tube 905 attached to the fan 920 and the nozzle manifold 910 may be removable from the frame. In this latter embodiment, a relatively long tube/hose 950 may be attached to the fogger 900 which may be moved by an individual to an area requiring the fine droplets 912. FIG. 5 illustrates another system 1000" in accordance with example embodiments. In FIG. 5, the system 1000" may be substantially identical to the systems 1000 and 1000' except that a hose reel 975 may be provided to wrap the hose 950 around.

FIG. 6 is another example of a system 1000'" in accordance with example embodiments. In FIG. 6 the system 1000'" may be substantially identical to the previously described systems 1000, 1000', and 1000" except that the system 1000'" may include a plurality of foggers 900-1 and 900-2 comprised of a plurality of tubes 905-1 and 905-2 housing a plurality of fans 920-1 and 920-2 and a plurality of nozzle manifolds 910-1 and 910-2. Although FIG. 6 only shows the plurality of tubes, fans and manifolds as including two tubes, fans, and manifolds, the invention is not limited thereto as the system 1000'" may include more than two foggers 900-1 and 900-2. In example embodiments, liquid pumped by the pump 200 may flow to a “T” fitting 700-2 which guides the liquid to one of, or both of the foggers 900-1 and 900-2. Although the embodiment of FIG. 6 uses a “T” fitting 700-2 to split the flow, another fitting, such as a “Y” or another type of fitting may be used in lieu of the fitting 700-2.

In example embodiments, the amount of fine droplets 912 produced by any of the disclosed systems 1000, 1000', 1000" and 1000'" may be controlled by altering the pressure of the system. If the pressure is increased more fine droplets 912 may be produced. In example embodiments, the pressure may be adjusted several ways. For example, the pressure may be adjusted by adjusting the pressure regulator 500. In example embodiments, the pressure regulator 500 may be a remote adjustable pressure regulator which may be remotely controlled by a user. As another example, an apparatus may be attached to the pump 200 that will stop, start, or slow the speed of the pump in order to maintain pressure. In this latter embodiment, the apparatus may be remotely controlled. As yet another example, the actuator 300 may be a remotely controlled motor. Increasing and or decreasing the actuator 300 may increase or decrease the pressure in the systems. Also, in example embodiments, a speed sensor may be incorporated in the systems 1000, 1000', 1000", and 1000' which detects the speed of the fluid flowing through the systems 1000, 1000', 1000", and 1000'". In this latter embodiment, the speed sensor may send a signal to a processor which controls the actuator 300 thus allowing for an automatic control of the systems. Also, the sensor may send a signal to a user controlling the systems 1000, 1000', 1000", and 1000'" which may indicate to the user whether to increase or decrease the speed at which the actuator 300 is operating. The amount of droplets produced may also be controlled by the addition or reduction of nozzles producing droplets 30 microns or less. The amount of droplets produced 30 microns or less may also be controlled by a combination of changing pressure, manually or remotely, as well as varying the amount of nozzles being used. In this case nozzles may be physically removed or controlled by a manual and remote on/off valve.

In example embodiments, the systems 1000, 1000', 1000", and 1000' may be used to treat a relatively large space which may or may not be an open space. For example, the systems 1000, 1000', 1000", and 1000' may be used to treat a relatively large room in a building or an outdoor area. For example, in example embodiments the systems 1000, 1000', 1000", and 1000' may be used to deliver a mosquito killer to kill mosquitoes inhabiting a neighborhood. Because the systems 1000, 1000', 1000", and 1000' may be used to treat relatively large areas, the systems 1000, 1000', 1000", and 1000' may require a relatively high volume of liquid to be dispersed as a fog. Furthermore, in example embodiments, the fog may be produced in a manner such that the fog does not contain charged particles.

Example embodiments of the invention have been described in an illustrative manner. It is to be understood that the terminology that has been used is intended to be in the nature of words of description rather than of limitation. Many modifications and variations of example embodiments are possible in light of the above teachings. Therefore, within the scope of the appended claims, the present invention may be practiced otherwise than as specifically described.

We claim:

1. A system comprising:
   a holding tank configured to hold a liquid;
   a pump configured to receive the liquid from the holding tank;
   a nozzle configured to emit a fog;
   a fan configured to move the fog; and
   a pressure regulator between the pump and the nozzle, wherein the pressure regulator is configured to have a set pressure of about 250 psi to about 3000 psi.

2. The system according to claim 1, further comprising:
   a motor configured to actuate the pump.

3. The system according to claim 2, wherein the motor is an electric motor.

4. The system according to claim 1, further comprising:
   a return line, wherein the system is configured to return the liquid pumped by the pump to the holding tank via the return line if the pressure of the liquid is above the set pressure.

5. The system according to claim 1, further comprising:
   an on/off valve between the nozzle and the pump.

6. The system according to claim 1, further comprising:
   a tube configured to direct a flow of air from the fan to the nozzle.

7. The system according to claim 6, wherein the nozzle is arranged at a first end of the tube and the fan is arranged at a second end of the tube.

8. The system according to claim 6, further comprising:
   a retractable high pressure hose between the nozzle and the pump.

9. The system according to claim 1, wherein the regulator is a remote adjustable pressure regulator.

10. The system according to claim 1, further comprising:
    a remote controlled reduction mechanism attached to the pump to remotely control a speed of the pump.

11. The system of claim 1, wherein the nozzle is configured to convert the liquid to fog using pressure alone.

12. A method comprising:
    transferring liquid from a holding tank to a pump;
    pumping the liquid to a pressure regulator;
    moving the liquid from the pressure regulator back to the holding tank when a pressure is above a first value and moving the liquid from the pressure regulator to a fogger when the pressure is below the first value; and
    creating a fog, wherein the pressure regulator between the pump and the fogger, wherein the pressure regulator is configured to have a set pressure of about 250 psi to about 3000 psi.

13. The method of claim 12, further comprising:
    blowing the fog out of a tube using a fan.

14. The method of claim 13, further comprising:
    remotely controlling the pump.

15. The method of claim 13, further comprising:
    remotely controlling a pressure regulator.

16. The method of claim 12, wherein the liquid includes at least one of a pesticide, an antimicrobial agent, and disinfectant.

\* \* \* \* \*